United States Patent [19]
Nadler et al.

[11] Patent Number: 5,336,473
[45] Date of Patent: Aug. 9, 1994

[54] STRIPPER-REACTOR FOR VOLATILE COBALT RECOVERY

[75] Inventors: Kirk C. Nadler, Baton Rouge; Thomas R. Broussard, Pride; Joseph K. Pitre, Baton Rouge, all of La.

[73] Assignee: Exxon Chemical Patents Inc., Linden, N.J.

[21] Appl. No.: 60,187

[22] Filed: May 11, 1993

Related U.S. Application Data

[62] Division of Ser. No. 891,339, May 29, 1992, Pat. No. 5,235,112.

[51] Int. Cl.$^5$ .................. B01J 10/00; C07C 45/00
[52] U.S. Cl. .................. 422/193; 203/DIG. 6; 203/49; 422/188; 422/234; 422/256; 568/453; 568/492
[58] Field of Search ............... 422/256, 234, 187–189, 422/193; 568/429, 451, 453, 438, 492; 203/49, DIG. 6

[56] References Cited

U.S. PATENT DOCUMENTS

| | | | |
|---|---|---|---|
| 3,868,422 | 2/1975 | Hart et al. | 568/453 |
| 4,625,067 | 11/1986 | Hanin | 568/451 |
| 4,982,024 | 1/1991 | Lin et al. | 206/DIG. 6 |

Primary Examiner—Robert J. Warden
Assistant Examiner—L. M. Crawford
Attorney, Agent, or Firm—John J. Mahon

[57] ABSTRACT

An apparatus for removing cobalt values from the crude product of a cobalt-catalyzed hydroformylation reaction wherein an overhead stripper-reactor reflux product is recycled to a location on the stripper-reactor which is capable of forming a stripping zone in the upper portion of the stripper-reactor and a reaction zone in the lower portion of the stripper-reactor.

4 Claims, 2 Drawing Sheets

STRIPPER-REACTOR FOR VOLATILE COBALT RECOVERY

This is a division of application Ser. No. 891,339, filed May 29, 1992, now U.S. Pat. No. 5,235,112.

The present invention relates generally to a method of removing dissolved cobalt compounds from the products of a cobalt catalyzed hydroformylation reaction wherein the reflux line is returned to the stripper-reactor at a location which is capable of forming a stripping zone and a reaction zone within the reactor chamber.

BACKGROUND OF THE INVENTION

Hydroformylation reactions involve the preparation of oxygenated organic compounds by the reaction of carbon monoxide and hydrogen (i.e., syn or synthesis gas) with carbon compounds containing olefinic unsaturation. The reaction is performed in the presence of a carbonylation catalyst and results in the formation of a compound, for example an aldehyde, which has one more carbon atom in its molecular structure than the starting olefinic feedstock. By way of example, higher alcohols may be produced in the so-called "oxo" process by hydroformylation of commercial $C_6$–$C_{12}$ olefin fractions to an aldehyde-containing oxonation product, which on hydrogenation yields respective $C_7$–$C_{13}$ saturated alcohols. The crude product of the hydroformylation reaction will contain catalyst, aldehydes, alcohols, unreacted olefin feed, syn gas and by-products.

Before further processing of the crude product is possible, it is necessary to remove the catalyst therefrom. One conventional method of removing cobalt values from such a crude product is to treat the product with an alkali or acid wash technique. See U.S. Pat. No. 3,725,534 (Reisch), which issued on Apr. 3, 1973. However, this approach uses expensive raw materials and incurs problems associated with finally removing essentially all traces of cobalt from the water wash streams before being discharged.

Another conventional method involves the oxidation of the cobalt catalytic species followed by extraction as a salt in aqueous solution. See U.S. Pat. No. 2,744,921 (Mertzweiller et al.), which issued on May 8, 1956.

U.S. Pat. No. 4,625,067 (Hanin), which issued on Nov. 25, 1986, discloses what is commonly referred to as the "Cobalt Flash" method. Cobalt Flash involves the contacting of the crude product with a stream of stripping gas to entrain volatile cobalt compounds. The contacting is performed in the presence of water and aqueous acid to dissolve those cobalt values not entrained in the gas under the conditions of temperature and pressure employed for the contacting, and the aqueous phase is subsequently separated from the organic hydroformylation reaction product.

U.S. Pat. No. 3,868,422, which issued on Feb. 25, 1975, and Great Britain Patent No. 893,524, which issued in 1962, are also directed to cobalt catalyst removal cycles which involve the stripping of volatile hydridocobalt carbonyl from crude oxo reaction products.

The goal of any stripper-reactor is two-fold. First, it must remove as much cobalt as possible from the oxo product, and second, it must maximize the percent of volatile cobalt recovered overhead. The first goal is important for meeting product quality specifications, maximizing the hydrogenation catalyst life, and avoiding cobalt losses. The second is important for improved oxo reactor performance and for minimizing the amount aqueous cobalt salts which must be recycled to oxo.

The present invention is an improvement over known stripping devices. Typical strippers recycle the reflux product to the top portion of the stripper, thereby forming what the present inventors have discovered is a single zone reactor chamber wherein the entire stripper functions as both a stripper and reactor.

The present inventors have developed, through extensive comparative experimentation, a stripper-reactor which is capable of carrying out the Cobalt Flash stripping process more efficiently, i.e., volatile cobalt recovery is substantially increased. This novel stripper-reactor increases volatile cobalt recovery by approximately 5–10% over conventional stripper which recycle reflux to the top portion of the stripper. Cobalt recovery is substantially increased by the formation of distinct stripper and reaction zones within the stripper-reactor. The present inventors have discovered, as demonstrated in the comparative examples below, that the location of the reflux recycle within the stripper-reactor is extremely critical in improving the recovery of volatile cobalt during the cobalt Flash process. Moreover, it was highly unexpected that the location of the reflux recycle on the stripper-reactor would provide such a marked increase in volatile cobalt recovery. It is believed that volatile cobalt recovery is greatly enhanced because volatile cobalt in the pure stripping zone is rapidly removed before it decomposes to nonvolatile $Co_2(CO)_8$ which can cause a decrease in overhead cobalt recovery.

To the contrary, conventional stripping devices typically recycle reflux product to the top of the reactor thereby forming a single combined stripping and reaction zone within the reactor chamber. This single zone allows for the undesirable decomposition of $HCo(CO)_4$ to $Co_2(CO)_8$ which decreases the overhead volatile cobalt recovery. This is primarily due to the longer retention time of volatile cobalt within the stripper-reactor.

The present inventors have also discovered that the water and organic acid feed port location about the Cobalt Flash system can slightly increase overhead volatile cobalt recovery as well.

The present invention also provides many additional advantages which shall become apparent as described below.

SUMMARY OF THE INVENTION

A novel stripper-reactor capable of removing volatile cobalt from a crude product of a cobalt-catalyzed hydroformylation reaction. The stripper-reactor includes an upper stripper section, an intermediate stripper section and a lower stripper section.

It is an object of the present invention that the stripper-reactor comprises: a means for feeding the crude product to the stripper-reactor; a means for feeding a stripping gas to the stripper-reactor such that the crude product is contacted with the stripping gas thereby entraining volatile cobalt compounds within the stripping gas, whereby the entrained volatile cobalt compounds are taken out overhead and organic hydroformylation reaction products and water containing water soluble cobaltous salts are taken out as bottoms, i.e., either an organic hydroformylation reaction product or an alcohol product depending upon the make-up of the crude product feed; a means for withdrawing the organic hydroformylation reaction products and water containing water soluble cobaltous salts; a means for withdrawing the stripping gas with the entrained volatile cobalt compounds from the stripper-reactor and delivering the stripping gas to an external refluxing means to produce a concentrated volatile cobalt product and a reflux product which comprises water, organics and dissolved carbonyls; and a means for recycling the reflux product to a location on the stripper-reactor which is capable of forming a stripping zone in the upper portion of the stripper-reactor and a reaction zone in the lower portion of the stripper-reactor.

A further object is a method for removing cobalt values from the crude product of a cobalt-catalyzed hydroformylation reaction which comprises: contacting the crude product in a stripper-reactor with a stream of stripping gas in the presence of water and organic acid to entrain volatile cobalt compounds in the stripping gas, whereby the entrained volatile cobalt compounds are taken out overhead and organic hydroformylation reaction products and water containing water soluble cobaltous salts are taken out as bottoms; withdrawing the organic hydroformylation products and water containing water soluble cobaltous salts from the stripper-reactor; withdrawing the stripping gas with entrained volatile cobalt compounds from the stripper-reactor; refluxing the withdrawn stripping gas with entrained volatile cobalt compounds thereby producing a concentrated volatile cobalt product and a reflux product; withdrawing the concentrated volatile cobalt product from the reflux means; and recycling the reflux product to a location on the stripper-reactor which is capable of forming a stripping zone in the upper portion of the stripper-reactor and a reaction zone in the lower portion of the stripper-reactor.

It is also an object to provide a method for producing higher aldehydes and higher alcohols which comprises: hydroformylating an olefinic feedstock with synthesis gas in the presence of a cobalt-containing catalyst to form a crude product mixture containing higher aldehyde, higher alcohol, secondary products and dissolved cobalt catalysts; removing the cobalt catalysts from the crude product by means of the novel stripper-reactor of the present invention; withdrawing the bottoms of the stripper-reactor and separating an organic product, e.g., organic hydroformylation reaction products or alcohol products, from the water containing water soluble cobaltous salt; recovering the concentrated volatile cobalt product and contacting the concentrated volatile cobalt product with the liquid olefinic feedstock to dissolve the cobalt compounds therein; and recycling the contacted liquid olefinic feedstock to the hydroformylation step.

Other and further objects, advantages and features of the present invention will be understood by reference to the following specification in conjunction with the annexed drawings, wherein like parts have been given like numbers.

DESCRIPTION OF THE PREFERRED EMBODIMENTS

Cobalt Flash is an environmentally clean process for recycling the cobalt catalyst used in oxo alcohol production. The Cobalt Flash concept is to recycle the cobalt catalyst by stripping it out of crude product. The crude product is typically delivered from an oxo reactor, although it is contemplated hereunder that any crude product feed containing cobalt products may be used as the feed in accordance with this invention.

The cobalt catalyst is stripped out at low pressure as catalytically active and volatile $HCo(CO)_4$. The active cobalt is then absorbed into an olefin which becomes the fresh feed for oxonation. Any remaining cobalt which is not stripped is recovered as bottoms and recycled to the oxo process as aqueous cobalt formate. Instrumental in the Cobalt Flash catalyst removal process is the stripper-reactor, where the volatile cobalt is removed from the crude product feed. The stripper-reactor operation is considered efficient when it maximizes the percentage of the total cobalt recovered as $HCo(CO)_4$ and minimizes the residual cobalt left in the crude product feed.

In order to maximize the volatile cobalt recovery efficiency, the present inventors undertook a thorough investigation of the effects of nine independent stripper-reactor design options and their effect on stripper-reactor performance. These design options are the reboiler temperature, the condenser temperature, the feed temperature, the oil to water ratio, the gas to liquid ratio, the formic acid concentration, the pressure, the reflux location, and the water injection location. It was discovered during these experiments that the reflux location exhibited a marked effect on total volatile cobalt recovery. To a lesser extent the water and organic acid injection location also effected the overhead volatile cobalt recovery.

Figure 1:
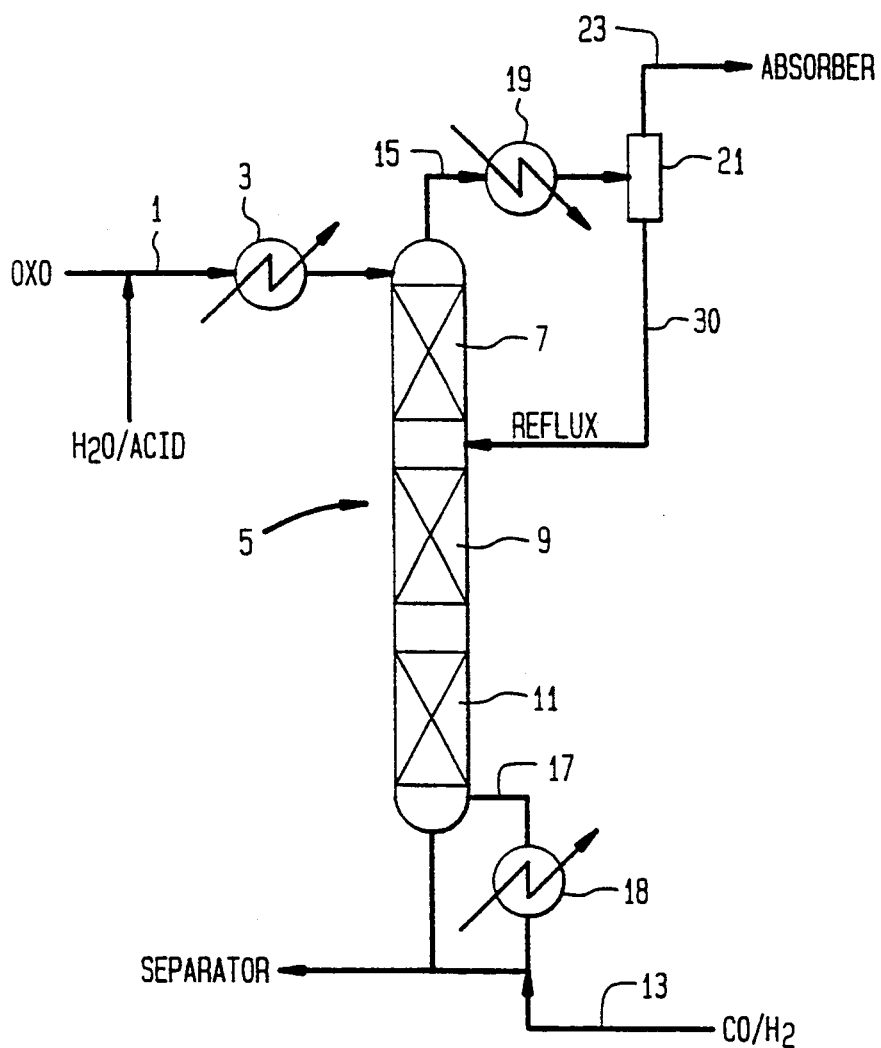
FIG. 1 is a schematic representation of the stripper-reactor used in volatile cobalt recovery in accordance with the present invention wherein the reflux line is returned to the intermediate stripper section of the stripper-reactor and wherein water and acid are injected into the crude product feed.
Figure 2:
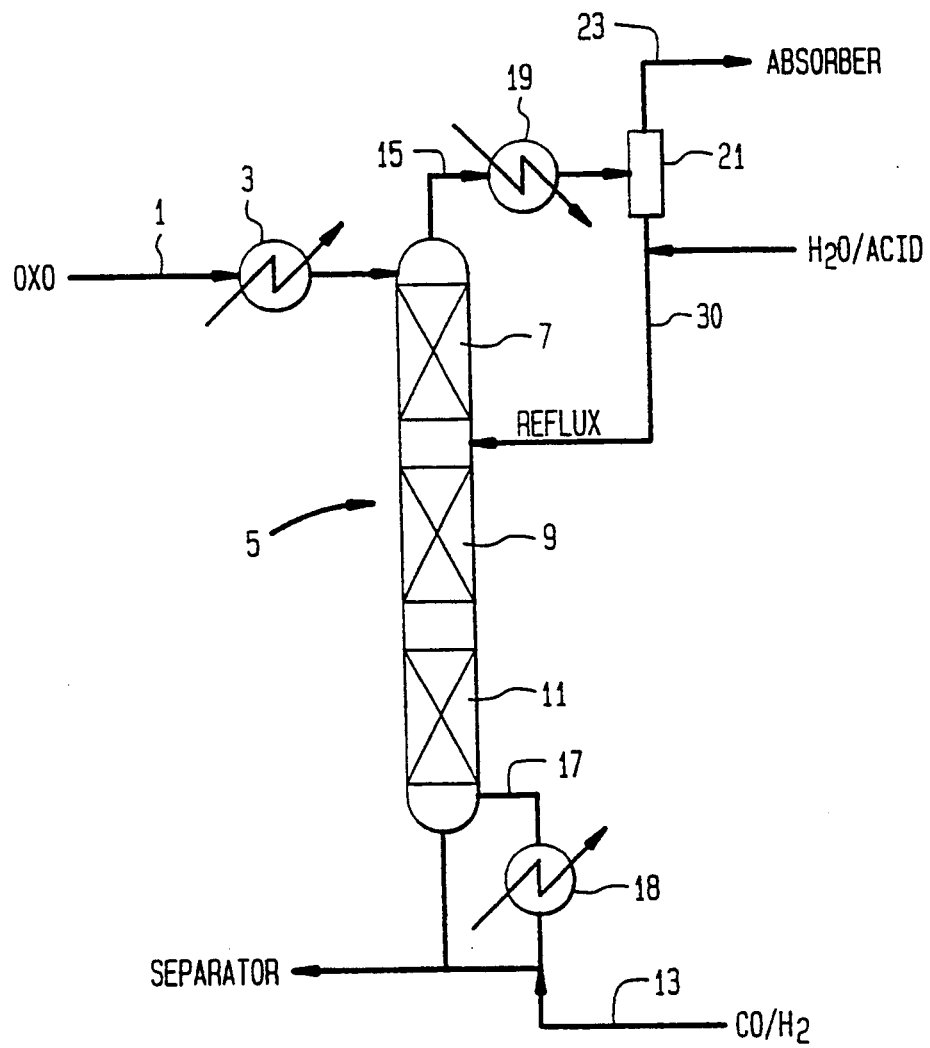
FIG. 2 is a schematic representation of the stripper-reactor used in volatile cobalt recovery in accordance with the present invention wherein the reflux line is returned to the intermediate stripper section of the stripper-reactor and wherein water and acid are injected into the reflux product.

The present invention can best be describe by referring to the attached drawings, wherein FIGS. 1 and 2 are directed to the stripper-reactor used, for example, in a Cobalt Flash catalyst removal process. In accordance with the embodiment shown in FIG. 1, crude oxo product containing cobalt is mixed with water and an organic acid, e.g., formic acid, and the resulting two-phase mixture is sent via conduit 1 to the top or stripper-reactor 5. Stripper-reactor 5 having an upper stripper section 7, an intermediate stripper section 9 and a lower stripper section 11. Preheated stripping gas, e.g., syn gas, feed via conduit 13 to the bottom of stripper-reactor 5 such that it flows up through reactor 5 and strips $HCo(CO)_4$ (i.e., entrained volatile cobalt compounds) from the crude oxo product and carries it overhead in the vapor stream to an absorber (not shown). In the absorber, the $HCo(CO)_4$ is absorbed from the gas stream into a fresh olefin. The cobalt-loaded olefin is then used as feed to the oxo reactors.

Prior to delivering the entrained volatile cobalt compounds to the absorber, they are carried via conduit 15 to heat exchanger 19 and reflux unit 21 wherein $HCo(CO)_4$ is taken overhead via conduit 23 to the absorber and a reflux product comprising water, organics and dissolved cobalt carbonyls is taken as bottoms. The reflux product is then recycled via reflux line 30 to a location on stripper-reactor 5 which is capable of forming a stripping zone in the upper portion of the stripper-reactor and a reaction zone in the lower portion of the stripper-reactor, i.e., intermediate stripper section 9. Preferably, the stripping zone is formed in about the top one-third of stripper-reactor 5 and the reaction zone is formed in about the bottom two-thirds of stripper-reactor 5.

It is preferable that reflux line 30 have a recycle port disposed near the top of intermediate stripper section 9 such that upper stripper section 7 forms a stripping zone, and intermediate stripper section 9 and lower stripper section 11 form a reaction zone. It should be noted that although the stripping zone functions as a pure stripper section, the reaction zone typically functions as both a reaction and stripper section.

The two-phase liquid removed as bottoms from the stripper-reactor via conduit 17 is preferably reduced in temperature by cooler 18 and thereafter separated by an oil-water separator (not shown). The aqueous phase typically includes water, dissolved cobalt formate (i.e., water soluble cobaltous salt), and formic acid. The organic phase typically includes aldehyde, dissolved water, and some formic acid. However, the constituent make-up of these phases will certainly differ depending upon the crude product feed injected into the stripper-reactor. If necessary, the organic phase is water washed to remove residual cobalt and thereafter sent to either hydrogenation or distillation.

At oxo reaction conditions (e.g., $2.068 \times 10^2$ bars (3000 psig), 1:1 syn gas, 149° C.) cobalt carbonyls are present mainly as $HCo(CO)_4$. Based on literature estimates and spectroscopic measurements, the percentage of total cobalt present as $HCo(CO)_4$ is probably from 70–90%, with the remainder being $Co_2(CO)_8$. As long as the pressure remains high, $HCo(CO)_4$ and $Co_2(CO)_8$ are probably the only cobalt species present in the reaction mixture.

As temperature and pressure are reduced, $HCo(CO)_4$ is less thermodynamically favored, and it decomposes to form $Co_2(CO)_8$ and hydrogen. Likewise, $Co_2(CO)_8$ is unstable at low CO partial pressure, and it forms $[CoB_6]^{9+}[Co(CO)_4]^{-}{}_2$ in the presence of dissolved or free water or alcohols (where B=ROH or $H_2O$). These reactions occur fairly rapidly, and their net effect is to reduce the amount of $HCo(CO)_4$ available in the reaction mixture by converting it to non-volatile forms of cobalt.

The cobalt which is converted to $[CoB_6]^{2+}[Co(CO)_4]^{-}{}_2$ is transferred to the aqueous phase in the cobalt flash stripper-reactor. In the water, protons from formic acid are available to convert the cobalt carbonyl anion back to $HCo(CO)_4$. This $HCo(CO)_4$ can be removed from the system as a volatile gas or decompose to $Co_2(CO)_8$ once again.

The present inventors have discovered that recovery of $HCo(CO)_4$ in the Cobalt Flash process can be maximized in one of two ways. The first is to minimize the residence time between oxo and the stripper-reactor. If the $HCo(CO)_4$ is not given time to decompose during transit to Cobalt Flash, then it is available for immediate stripping into the gas phase. The second way is to maximize the stripping efficiency of the stripper-reactor itself so as to ensure that $HCo(CO)_4$ does not spend much time in the liquid phase in the stripper-reactor. Once it is formed, $HCo(CO)_4$ should be removed as rapidly as possible so that it does not have time to decompose. Each time one mole of $HCo(CO)_4$ decomposes to $Co_2(CO)_8$, the $Co_2(CO)_8$ forms $[CoB_6]^{2+}[Co(CO)_4]^{-}{}_2$, and one third mole of cobalt ends up as aqueous $Co^{2+}$.

The following examples demonstrate how modifications to two design parameters of the stripper-reactor maximize the stripping efficiency of the stripper-reactor itself so as to ensure that $HCo(CO)_4$ does not spend much time in the liquid phase in the stripper-reactor. The two design parameters are reflux recycle location, and acid and water injection location.

EXAMPLE 1

A Cobalt Flash stripper-reactor (S/R) was built with three different locations for returning the reflux product to the reactor, i.e., at the top of the reactor (i.e., upper stripper section), one-third of the way down the reactor (i.e., intermediate stripper section), and two-thirds of the way down the reactor (i.e., lower stripper section). Nine sets of experiments were conducted in which only the reflux location changed as other operating variables were held constant. The results are set forth below in Table 1.

TABLE 1

(EFFECT OF REFLUX LOCATION ON S/R PERFORMANCE)

| Run # | Olefin Grade | Reflux Location | Cobalt % Overhead | Cobalt ppm in Product |
|---|---|---|---|---|
| 1a | C12 | Upper | 73.7 | 14 |
| 1b | C12 | Intermediate | 75.8 | 22 |
| 1c | C12 | Lower | 74.9 | 8 |
| 2a | C9 | Upper | 70.2 | 41 |
| 2b | C9 | Intermediate | 76.2 | 12 |
| 2c | C9 | Lower | 80.4 | 23 |
| 3a | C9 | Intermediate | 73.3 | 32 |
| 3b | C9 | Lower | 70.7 | 31 |
| 4a | C9 | Intermediate | 74.9 | 26 |
| 4b | C9 | Lower | 77.2 | 30 |
| 5a | C9 | Upper | 53.8 | 64 |
| 5b | C9 | Intermediate | 69.8 | 32 |
| 5c | C9 | Lower | 66.5 | 107 |
| 6a | C9 | Intermediate | 74.7 | 34 |
| 6b | C9 | Lower | 72.7 | 63 |
| 7a | C5,7 mix | Intermediate | 48.6 | 239 |
| 7b | C5,7 mix | Lower | 34.7 | 255 |
| 8a | C7 | Intermediate | 69.4 | 29 |
| 8b | C7 | Lower | 56.4 | 87 |
| 9a | C8 | Intermediate | 77.2 | 38 |
| 9b | C8 | Lower | 69.3 | 66 |

Based upon the above data, it is abundantly clear that when the reflux product is recycled back to the intermediate stripper section of the stripper-reactor the stripping efficiency of the stripper-reactor itself is maximized so as to ensure that $HCo(CO)_4$ does not spend much time in the liquid phase in the stripper-reactor. When the reflux product is recycled to the lower stripper section there is a greater chance of carbonyl breakthrough in the hydroformylation product. Moreover, when the reflux product is recycled to the upper stripper section the percent of volatile cobalt removed overhead is consistently lower than that removed when recycled to the intermediate stripper section. Recycling to the upper stripper section also tended on average to increase the cobalt in the hydroformylation product which is also undesirable.

EXAMPLE 2

Several tests were conducted to determine the effect of injecting the water and acid into the reflux product versus injecting the water and acid into the crude product feed. During each of the below tests, the reflux product was injected into the intermediate stripper section.

TABLE 2

(WATER AND ACID INJECTION LOCATIONS)

| Run # | Olefin Grade | Injection Location | Cobalt % Overhead | Cobalt ppm in Product |
|---|---|---|---|---|
| 1a | C7 | Feed | 65.9 | 48 |
| 1b | C7 | Reflux | 63.3 | 62 |
| 2a | C9 | Feed | 69.5 | 31 |
| 2b | C9 | Reflux | 71.5 | 25 |
| 3a | C8 | Feed | 63.1 | 0 |
| 3b | C8 | Feed | 71.2 | 0 |
| 3c | C8 | Reflux | 73.9 | 12 |

The injection location does not make a large difference in stripper-reactor performance. There does appear to be slightly higher volatile cobalt recovery when the water and acid are mixed with the reflux product. However, without water injection in the crude product feed, it is likely that preheater 3 would plug with cobalt formate. For this reason, the recommended injection location is in the crude product feed, even with the slight debit in overhead volatile cobalt recovery. If there is no crude product feed preheater, then it is acceptable to inject water and acid into the reflux line.

Optionally, the stripper-reactor of the present invention can be used to remove volatile cobalt from other crude product feeds generated during the oxo process. For example, crude products can be delivered to the stripper-reactor from a preformer reactor absent any significant quantities of organic hydroformylation reaction products. The crude product feed from the preformer reactor may include, for example, dicobalt octacarbonyl, formic acid, hydridocobalt tetracarbonyl, organics, and water. In this instance, volatile cobalt compounds would still be entrained in the syn gas and taken overhead, but the bottoms would comprise organic hydroformylation reaction products and water containing water soluble cobaltous salts.

FIG. 2 is a schematic representation of the stripper-reactor wherein the water and acid are injected together with the reflux product via reflux line 30.

The stripper-reactor is preferably operated at a temperature of not greater than 100° C. and at a pressure below 10.13 bars, the pressure being lower than the decomposition pressure of the cobalt compounds at the contacting temperature. The water and organic acid is added to the crude hydroformylation product feed in an amount in the range between about 5 to about 15% by weight, based on the organic content of the crude hydroformylation products. When the feed is a product from a preformer reactor, the water and organic acid is added thereto in an amount in the range between about 5 to about 50% by weight, based on the organic content of the crude alcohol product.

The organic acid is typically selected from the group consisting of: formic acid, acetic acid, propionic acid, and other acids having a boiling point approximately the same as water. The organic acid is preferably formic acid in an amount of from about 1 to about 5% by weight.

The volume ratio of the stripping gas to the crude product is from about 20:1 to about 250:1, as determined at the temperature and pressure used in the stripper-reactor. More preferably, the volume ratio is from about 50:1 to about 125:1.

The stripping gas is selected from synthesis gas, nitrogen and mixtures thereof. The contacting of the crude product with stripping gas in the stripper-reactor is preferably carried out at a pressure of from about to about 5.065 bars absolute and at a temperature from about 60° C. to about 100° C.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A stripper-reactor capable of removing volatile cobalt from a crude product of a cobalt-catalyzed hydroformylation reaction which comprises:
    a means for feeding said crude product to a stripper-reactor, said stripper-reactor comprising an intermediate stripper section disposed between an upper stripper section and a lower stripper section;
    a means for feeding a stripping gas to said stripper-reactor such that said crude product is contacted with said stripping gas thereby entraining volatile cobalt compounds within said stripping gas whereby the entrained volatile cobalt compounds are taken out overhead and organic hydroformylation reaction products and water containing water soluble cobaltous salts are taken out as bottoms;
    a means for withdrawing said organic hydroformylation reaction products and said water containing water soluble cobaltous salts from said stripper-reactor;
    a means for withdrawing the stripping gas with said entrained volatile cobalt compounds from said stripper-reactor and carrying it to an external refluxing means to produce a concentrated volatile cobalt product and a reflux product; and
    a means for recycling said reflux product to said intermediate stripper section via a reflux conduit, wherein a stripping zone is formed in said upper stripper section and a reaction zone is formed in said intermediate stripper section and said lower stripper section.

2. The stripper-reactor according to claim 1 wherein said stripping zone is formed in about the top one-third of said stripper-reactor and said reaction zone is formed in about the bottom two-thirds of stripper-reactor.

3. The stripper-reactor according to claim 1 further comprising a means capable of adding water and organic acid to said reflux product.

4. The stripper-reactor according to claim 1 further comprising a means capable of adding water and organic acid to said crude product.

* * * * *